(12) United States Patent
Wilson

(10) Patent No.: US 7,766,017 B2
(45) Date of Patent: Aug. 3, 2010

(54) ALTERED RANGE OF MOTION DEVICE

(76) Inventor: Anne Wilson, 17316 Highway 64, Anderson, AL (US) 35610

( * ) Notice: Subject to any disclaimer, the term of this patent is extended or adjusted under 35 U.S.C. 154(b) by 144 days.

(21) Appl. No.: 11/514,769

(22) Filed: Sep. 1, 2006

(65) Prior Publication Data

US 2008/0053464 A1    Mar. 6, 2008

(51) Int. Cl.
*A61B 19/00*    (2006.01)
*A61F 5/00*    (2006.01)
(52) U.S. Cl. .................................. 128/869; 602/19
(58) Field of Classification Search ......... 128/128–876, 128/878; 602/19, 1, 5
See application file for complete search history.

(56) References Cited

U.S. PATENT DOCUMENTS

| 1,219,453 | A | * | 3/1917 | Hansen | 128/878 |
| 3,901,229 | A | * | 8/1975 | Hensel et al. | 128/873 |
| 3,920,012 | A | * | 11/1975 | Patel | 128/849 |
| 5,031,639 | A | * | 7/1991 | Wolfer | 128/874 |
| 5,549,121 | A | * | 8/1996 | Vinci | 128/878 |
| 6,024,091 | A | * | 2/2000 | Bennett | 128/873 |

* cited by examiner

*Primary Examiner*—Patricia M Bianco
*Assistant Examiner*—Tarla R Patel
(74) *Attorney, Agent, or Firm*—David W. Barman; Robert M. Schwartz

(57) ABSTRACT

The device of the present invention is to prevent voluntarily or involuntarily arm movement that could be harmful to a medical patient during the patient's treatment using the patient's body weight to restrain the arms from movement.

5 Claims, 3 Drawing Sheets

ALTERED RANGE OF MOTION DEVICE

BACKGROUND OF THE INVENTION

The device was developed to address a need in the medical field to provide a means of restricting patients from voluntarily or involuntarily using their arms to disconnect tubes of medical equipment. In some cases, failure to restrain may result in further injury or hamper medical treatment.

There has been a recognized need to restrain the arms of a patient in a medical setting. The need for physical restraint is often to protect various articles that are attached during medical treatment. It is often imperative, if not dangerous, if any of these articles are moved or removed from their position in which they have been placed. When caring for a patient that is awake and alert, it is possible to explain to the patient the need to restrict their movements. But, when one has a patient that is unconscious and may exhibit involuntary motions, a restraint must be used. Further, it can be a shock for a person to suddenly awake from surgery or other medical influences and find an IV in their arm, feel a cervical collar around their neck, or any other medical device. Disturbing the positioning of these and other devices may be hazardous or even fatal. Additionally, patients that are in a weakened frame of mind or under certain medication may remove or attempt to remove medical devices or articles vital to their treatment or survival.

Previous articles have recognized the necessity of protecting and securing auxiliary equipment to a patient. Further, several patented articles employing straps have been proposed for addressing certain specific situations in the medical field.

U.S. Pat. No. 4,877,038, issued to Eberhard Fricke et al. on Oct. 31, 1989, describes a hand and arm restraint for patients. The restraint comprises a rectangular fabric panel having straps projecting from two corners and another, separate strap that can be passed through eyes located at the other two corners. This device requires the arms to be restrained in an awkward position across the front of the body.

U.S. Pat. No. 5,549,121, issued to Vincent A. Vinci on Aug. 27, 1996, describes an arm support comprising a flexible fabric intended to support a patient's arms during a medical diagnostic or remedial procedure. The fabric is formed as an elongate strip-bearing hook and loop fasteners at certain points, to enable the strip to be folded over and adhered to itself.

U.S. Pat. No. 5,558,102, issued to Andrew D. McCarthy on Sep. 24, 1996, describes a restraint harness comprised entirely of straps. The straps attach to one another at removable attachment points by buckles or loops. There is no base panel having attachment structure for the straps, as seen in the present invention.

U.S. Pat. No. 5,664,58.1, issued to John P. Ashley on Sep. 9, 1997, describes a securing strap intended to control intravenous tubing connected to an injection port. The securing strap comprises a relatively large base panel and two smaller straps. The smaller straps attach to the base panel by hook and loop fastener. Configuration and proportions of the components of the device of Ashley differ from those of the present invention.

U.S. Pat. No. 5,832,928, issued to James D. Padilla, Jr. on Nov. 10, 1998, describes a securement device for securing intravenous tubing on a patient. Upper and lower sections of the device are secured in place by straps bearing hook and loop fastener.

These devices, and others, each are deficient in that they do not provide for a secure arm restraint system that can hold the arm in a supine position. The restraint must be firm enough to immobilize yet not apply excessive force to the arms.

SUMMARY OF THE INVENTION

The apparatus of the present invention is an altered range of motion device that enables the patient to be restrained in comfort and safety.

In one embodiment, the apparatus for restraining the arms of a person comprising:

(a) a sleeve portion attaching around each arm;

(b) fastening means by which said sleeve portion is secured to each arm;

(c) a transverse portion extending under the torso of a person;

whereby the weight of said person lying on said transverse portion provides the necessary force to immobilize said person's arms.

The apparatus has sleeve portion that substantially covers the arm of the wearer and may have a fastening means that is hook and loop fastener commonly sold as VELCRO®, buttons, or snaps. Preferably, the apparatus is constructed of a flexible, washable, non-irritating fabric.

In a preferred embodiment, the apparatus of the subject invention secures the arms of the wearer in a supine position. This allows for a medical caregiver to access any objects or devices, such as intravenous tubes and the like, and protects these articles from accidental or purposeful removal by the patient.

In another embodiment, the apparatus for restraining the arms of a person, comprises a base panel, wherein said base panel is sufficiently long as to wrap almost entirely around an adult torso, and the width of said base panel is limited to half the length of said base panel.

The apparatus may further comprise multiple securing straps, wherein said straps each have width limited to one tenth of the length of said base panel.

In another embodiment, the current apparatus may further comprise straps that secure to the sides of a hospital bed. Typically, hospital beds have rails on either side. The apparatus may comprise straps that either extend from the underside of the patient or extend from the arm portions. In either configuration, the straps need to be long enough so that they may tie to either of the rails on the side of a conventional hospital bed or to some other suitable location.

In yet another embodiment, the current apparatus may further comprise a means by which the apparatus may be removed quickly in the event of an emergency. Such means may include but would not be limited to a zipper, a latch and the like.

Regarding the securing straps, at each end of the devise, they come to the center of the devise to form the channels that limit the range of motion of the arm.

The apparatus for restraining and containing the limbs of a medical patient and ancillary devices employed in medical procedures, may also comprise:

(a) a flexible base panel sufficiently long as to wrap almost entirely around an adult torso, wherein the width of said base panel is limited to half the length of said base having strip of connective material placed in the center portion of the panel. This center portion connects with the ends of the devise.

Also contemplated in the present invention is a method for restraining the limbs of a medical patient and protecting ancillary devices employed in medical procedures, comprising:

(a) fastening to a patient an apparatus having a flexible base panel having an upper side with one member of hook and loop fastener, and a lower side; a plurality of flexible straps each having one side covered with the complementing member of hook and loop material;

(b) securing the arms of patient in sleeve portion; wherein said sleeve portion is secured to said flexible base panel and further wherein said sleeve portion substantially immobilizes the arms of the wearer and secures the arms in a supine position.

It is an object of the present invention to provide an apparatus to restrain the range of motion in their arms.

It is another object of the present invention to provide a range of motion restraint such that the arms remain supine.

It is another object of the present invention to provide a range of motion restraint such that a patient is prevented from voluntarily or involuntarily interfering with medical devices attached to the patient's body.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

The present invention sets forth an apparatus for decreasing a patient's range of motion in the patient's arms. The apparatus restrains a medical patient by restraining the arms using fabric wrapped around the arms, connecting underneath the patient, while lying on a flat surface. The patient's body weight is used to immobilize the movement of the arms.

The apparatus frees the patient's hands, which allows the medical personnel to take pulse oximetry readings, capillary refill, and hand temperature. The medical personnel are also able to assess IV sites and thread tubing up the apparatus and away from patient's hands. The apparatus frees chest for maximum chest expansion, auscultation, electrodes, central lines, and chest tubes.

The apparatus allows for the patient to be turned from side to side in order to prevent things such as decubitus from forming as well as respiratory complications. The apparatus can be adjusted to different body types and can come in multiple sizes in order to accommodate larger or smaller patients.

Figure 1:
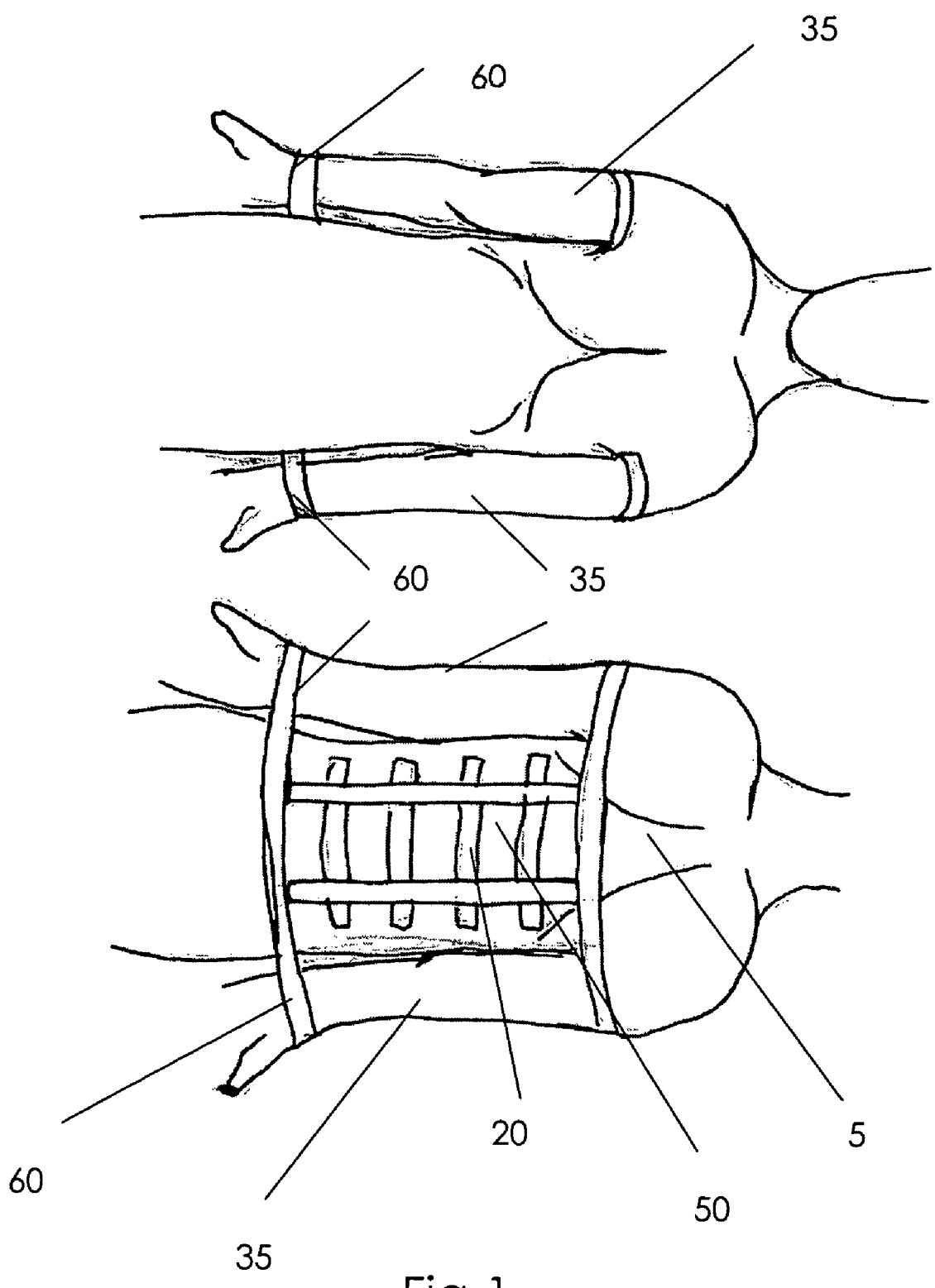
FIG. 1 is a perspective view showing a representative application of the invention in both anterior and posterior views while the apparatus is worn by a patient.

FIG. 1, shows the top view (anterior) perspective a patient wearing the apparatus whereby the arms are essentially immobilized in a supine position. The patient arms are placed within sleeves 35 and the hands extend through wrist strap 60 which extends from underneath the patient and uses the patient's own body weight to restrict range of motion. In one embodiment the wrist strap 60 may be adjustable such that a patient may be given more or less ability to move their arms depending on the individual circumstances. FIG. 1 also shows the back (posterior) view where depiction is shown that the arms are secured by the side of the patient. The patient 5 will lie on panel 50 that comprises straps 20 giving strength and support to the article.

Figure 2:
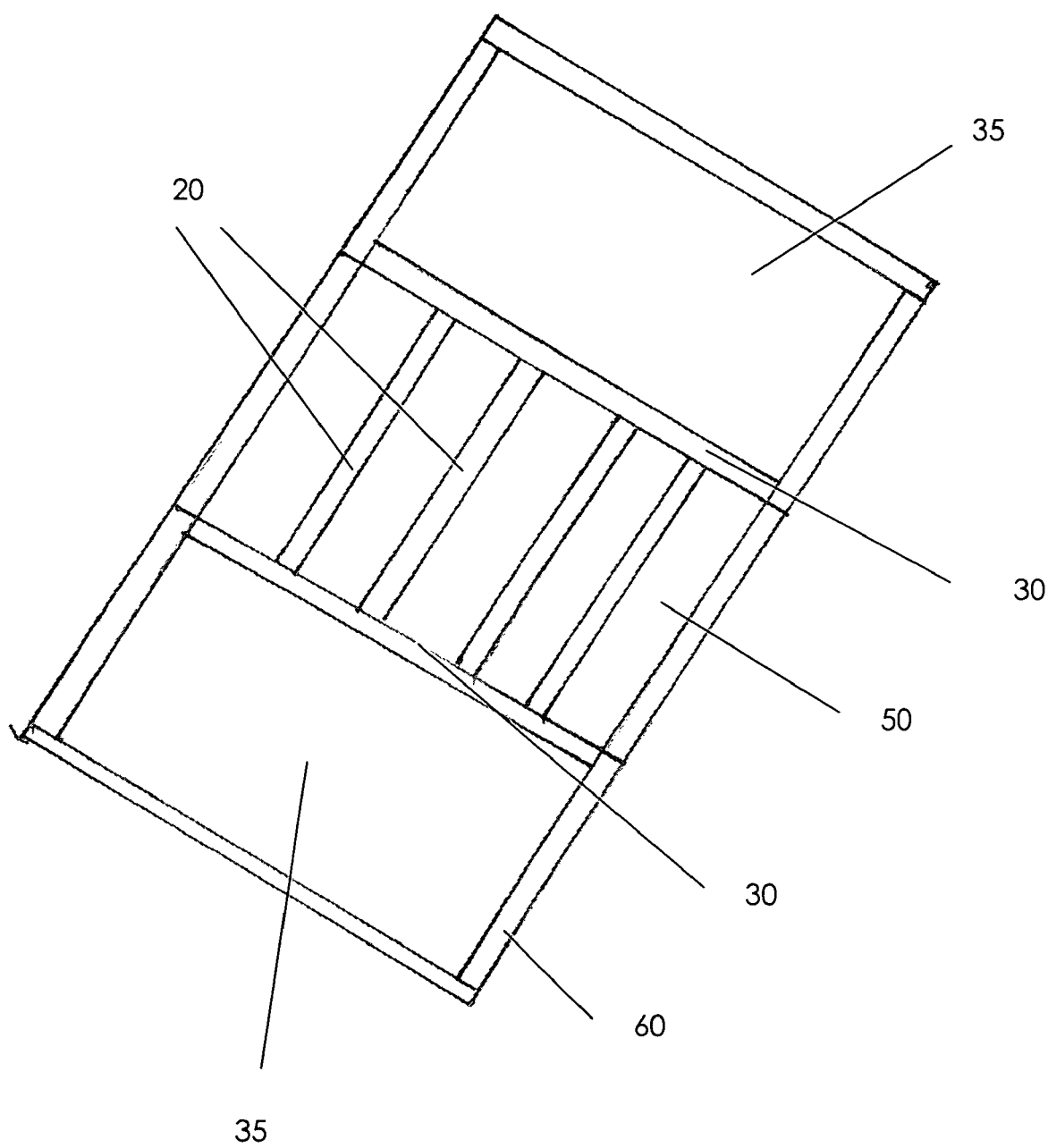
FIG. 2 is an exploded, top perspective view of the invention.

Turning now to FIG. 2, the novel apparatus comprises a generally rectangular panel 50 of flexible material. The rectangular material has terminal widths 10 that are looped to form a cavity for receiving the arms of the patient. There are flexible horizontal supports 20 and vertical supports 30. This configuration is highly useful in maintaining equilibrium and control when transporting a supine patient on a gurney.

Figure 3:
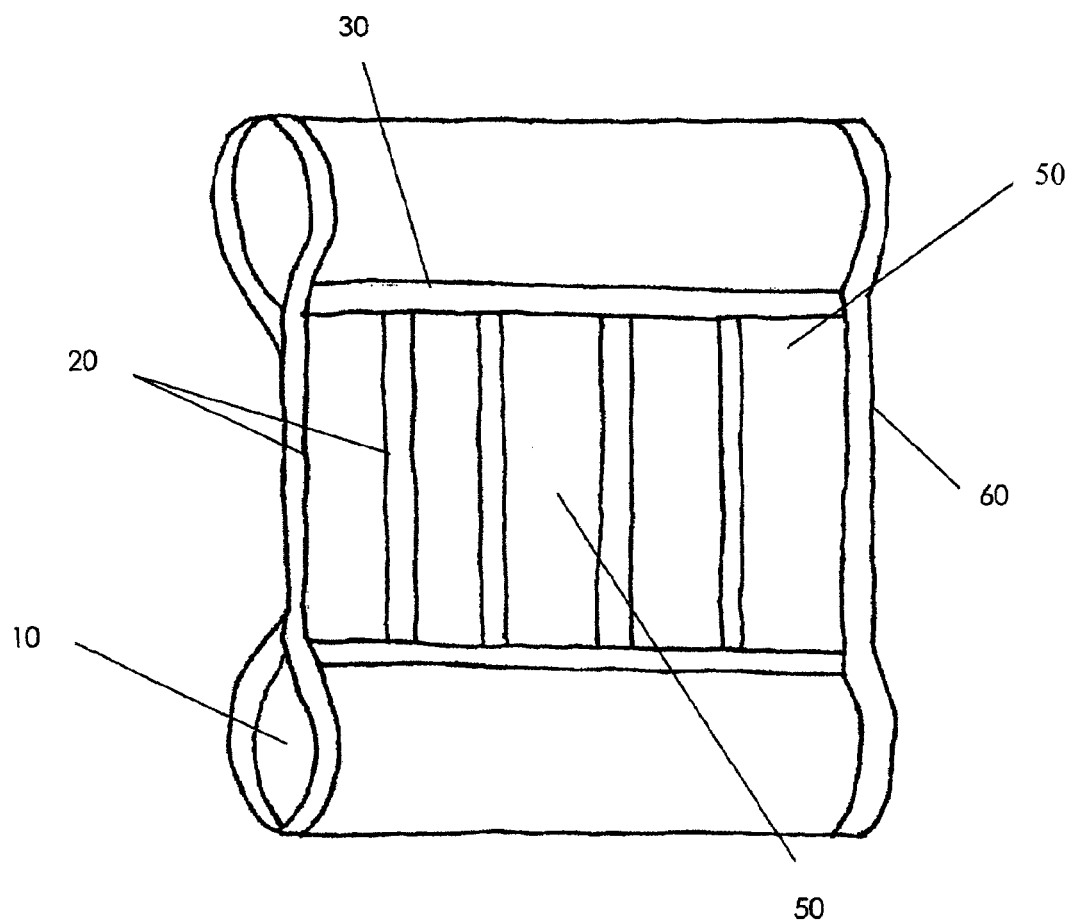
FIG. 3 is a top perspective view showing the openings for each arm.

Looking at FIG. 3, the panel 50, comprises vertical straps 20 and horizontal straps 30 that give strength and support to the article in use. The patient's arms will be inserted through Sleeves 10 and the hands will extend such that the wrists are surrounded by wrist strap 60.

Generally, the invention has been described in its preferred form or embodiment with some degree of particularity, it is to be understood that this description has been given only by way of example and that numerous changes in the details of construction, fabrication and use, including the combination and arrangement of parts, may be made without departing from the spirit and scope of the invention.

I claim:

1. An apparatus for restraining the arms of a person consisting essentially of:
   (a) a rectangular panel, said panel formed to wrap around a human torso; said panel having a terminal width on each side that is looped to form a cavity for receiving arms of a patient, the length of each cavity is attached along the entire width of said panel;
   (b) a plurality of flexible horizontal supports incorporated entirely within a peripheral boundary of said panel;
   (c) a plurality of flexible vertical supports incorporated entirely within a peripheral boundary of said panel; wherein each of said horizontal supports and vertical supports give strength and support to the apparatus such that the apparatus restrains the range of motion in the arms of a patient wearing the apparatus and immobilizes the arms of said patient using only the patient's body weight.

2. The apparatus according to claim 1, wherein said cavity substantially covers the arm of the wearer.

3. The apparatus according to claim 1, wherein said apparatus is primarily constructed of flexible, washable, non-irritating fabric.

4. The apparatus according to claim 1, wherein said apparatus restrains the arms of the wearer in a supine position.

5. A method for restraining the limbs of a medical patient and protecting ancillary devices employed in medical procedures, comprising:
   (a) providing an apparatus comprising rectangular panel, said panel formed to wrap around a human torso; said panel having a terminal width on each side that is looped to form a cavity, the length of each cavity is attached along the entire width of said panel for receiving the arms of a person within each; whereby said rectangular panel is a transverse portion extending under the torso of a person, said panel further a plurality of flexible horizontal supports incorporated entirely within peripheral boundary of said panel and a plurality of flexible vertical supports incorporated entirely within peripheral boundary of said panel having;
   (b) placing each of the arms of a patient in each respective cavity; and
   (c) lying a patient on their back such that said apparatus substantially immobilizes the arms of the wearer, said immobilization imparted only by the weight of said patient.

* * * * *